United States Patent [19]

Kathawala

[11] 4,089,908
[45] May 16, 1978

[54] SUBSTITUTED METHANOLS

[75] Inventor: Faizulla G. Kathawala, West Orange, N.J.

[73] Assignee: Sandoz, Inc., E. Hanover, N.J.

[21] Appl. No.: 682,087

[22] Filed: Apr. 30, 1976

Related U.S. Application Data

[63] Continuation of Ser. No. 480,054, Jun. 17, 1974, abandoned.

[51] Int. Cl.$^2$ ............................................. C07C 43/20
[52] U.S. Cl. ........................... 260/613 D; 260/613 R; 424/341; 568/808; 568/807; 568/812; 568/813
[58] Field of Search ............ 260/613 D, 618 E, 613 R

[56] References Cited

U.S. PATENT DOCUMENTS 3,929,902  12/1975  Galantay ..................... 260/612 R
3,969,415  7/1976   Galantay ..................... 260/613 D

OTHER PUBLICATIONS

Cadiot, Ann. Chim. (Paris) Series 13, vol. 1, (1956) 214–229.
Papa et al., J.A.C.S., vol. 76 (1954), 4446–4450.

*Primary Examiner*—Bernard Helfin
*Attorney, Agent, or Firm*—Gerald D. Sharkin; Richard E. Vila; Frederick H. Weinfeldt

[57] ABSTRACT

The compounds are 1-aryl-1-alknyl-1-(t-butyl)-substituted methanols, e.g. 3-(2'-naphthyl)-4,4-dimethyl-pent-1-yn-3-ol, are useful as hypolipidemic agents, and are prepared by reacting a 4-aryl-pivalophenone with a metallo-alkynyl reagent under Grignard reaction conditions.

5 Claims, No Drawings

SUBSTITUTED METHANOLS

This is a continuation of copending application Ser. No. 480,054, filed June 17, 1974 (now abandoned).

This invention relates to substituted methanol compounds, and more particularly to 1-aryl-1-alkynyl-1-(t-butyl)-substituted methanols, to their preparation, and intermediates in their preparation, as well as to pharmaceutical compositions containing such compounds and the pharmaceutical use of such compounds.

The substituted-methanols of this invention may be conveniently represented by the formula I:

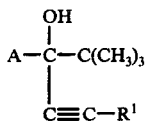   (I)

wherein
  $R^1$ is a hydrogen atom or alkyl having from 1 to 4 carbon atoms,
  A is a substituted or unsubstituted phenyl radical, or a 2'-naphthyl radical of the formulae

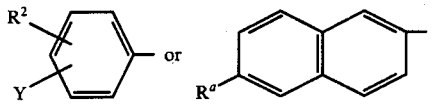

wherein
  Y is a hydrogen atom, alkyl having from 1 to 4 carbon atoms, alkoxy having from 1 to 18 carbon atoms, phenoxy or substituted or unsubstituted phenyl of the formula

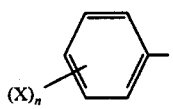

wherein
  X is a hydrogen atom, halo having an atomic weight of from about 19 to 36, i.e., fluoro, or chloro, alkoxy having from 1 to 4 carbon atoms or alkyl having from 1 to 4 carbon atoms, preferably a hydrogen atom;
  n is an integer from 1 to 2, preferably n is 1;
  $R^2$ is a hydrogen atom, alkyl having from 1 to 3 carbon atoms, or halo having an atomic weight of from about 19 to 35, i.e. fluoro or chloro; and
  $R^a$ is a hydrogen atom, halogen having an atomic weight of from about 19 to 36, i.e., fluoro or chloro, alkyl having from 1 to 4 carbon atoms, or alkoxy having from 1 to 4 carbon atoms;
provided that when Y is a hydrogen atom then $R^2$ is not fluoro, i.e. that when $R^2$ is fluoro then Y is other than a hydrogen atom.

With reference to the definitions of alkyl and alkoxy above, it is understood that when any of them have from 1 to 3 carbon atoms, the alkyl portion thereof may be methyl, ethyl, n-propyl or isopropyl, and when any of them have from 1 to 4 carbon atoms, the alkyl portion thereof includes the above enumerated alkyl groups as well as n-butyl, isobutyl and tertiary butyl. Where Y is alkoxy of 1 to 18 carbon atoms, two classes are contemplated, i.e., the class having from 1 to 4 carbon atoms (a lower alkyl moiety) and those having from 5 to 18 carbon atoms (i.e., a higher alkyl moiety, such as lauryl, myristyl or cetyl).

Preferred compounds are those wherein A is a para-substituted phenyl radical, and $R^a$ is a hydrogen atom, when A is a 2'-naphthyl radical.

Compounds I may be conveniently obtained by reacting (Process a) an aryl pivalophenone, of the formula II:

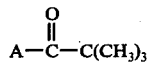   (II)

wherein
  A is as defined above with a metallo-alkynyl reagent of the formula III:

$$M—C\equiv C—R^1 \quad (III)$$

wherein
  $R^1$ is as defined above, and
  M is an equivalent cation of a reactive metal such as an alkali metal, e.g. lithium, sodium or potassium, or magnesium bromide or iodide, preferably lithium or magnesium bromide, in a suitable medium to obtain a "Grignard adduct" which is then hydrolyzed (Process b) to the corresponding Compound I.

Process (a) is carried out under conditions conventionally applied in carrying out Grignard reactions, e.g. moisture is essentially excluded by employing "dry" solvents and apparatus. Suitable solvents are those which are not detrimental to the reaction, generally aprotic organic solvents, such as ethers, e.g. diethyl ether or tetrahydrofuran. Suitable temperatures are from about 0° to 35° C., preferably from about 20° to 30° C. During the reaction, the alkyne corresponding to the alkynyl ($R^1$) moiety of the metallo-alkynyl reagent (a compound III) is preferably present, e.g. by bubbling through the reaction mixture in gaseous form.

Process (a) results in the formation of an intermediate ("Grignard adduct") which is the O-metallic salt of the corresponding compound I; the metallic cation being contributed by the metallo-alkyne reagent. Hydrolysis of the intermediate may be carried out in the manner conventionally used in hydrolyzing "Grignard adducts", i.e. in an aqueous medium, e.g., water or an aqueous acid or salt, such as dilute hydrochloric acid, or saturated aqueous sodium or ammonium chloride, e.g. at 20° to 30° C.

Compounds II and III used in the preparation of compounds I are known, some being available commercially, or where not known may be prepared by methods analogous to those described in the literature for the preparation of known compounds. For example, a compound II may be prepared by reacting a Grignard reagent of a compound of formula IV:

$$A—Br \quad (IV)$$

wherein
  A is as defined above, with trimethyl acetyl chloride, i.e. compound V:

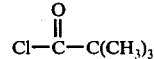   (V)

under conventional Grignard conditions and hydrolyzing the resultant intermediate as described above to the corresponding compounds II. When $R^1$ is a hydrogen atom, a convenient form of a compound III is lithium acetylide/ethylene diamine complex.

Compounds IV and V are known, or those compounds IV which are not known may be prepared in a manner analogous to those described in the literature for preparing the known compounds.

The above described procedure for preparing compounds I may conveniently be represented by Reaction Scheme A, below, wherein A, $R^1$ and M are as defined above:

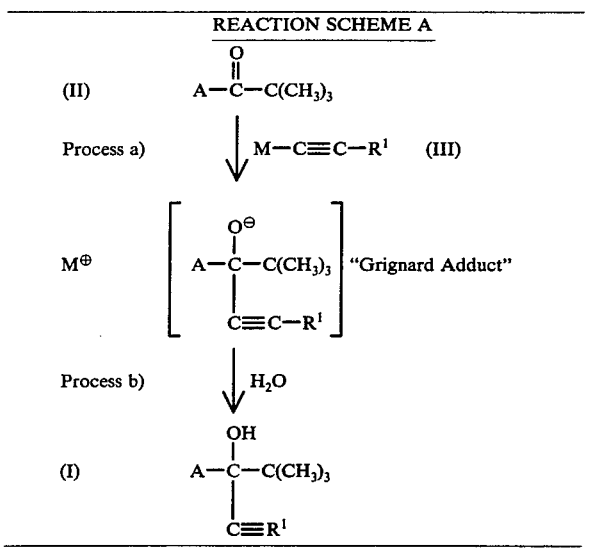

The compounds of structural formula (I) are useful because they possess pharmacological activity in animals. In particular, the compounds are useful as hypolipidemic agents, particularly hypolipoproteinemic agents, as evidenced, for example, by lowering cholesterol and triglyceride blood serum levels in tests on a group of white rats which are given typically 30–250 milligrams per kilogram of body weight per diem of the compound orally, for 6 days, followed by extraction with isopropanol of serum or plasma after anesthetizing the rats with sodium hexobarbital, and then noting the cholesterol and triglyceride contents as compared to those of a control group. The cholesterol and triglyceride contents are determined by the methods described by Lofland, H. B., Anal. Biochem. 9:393 (1964) : (Technicon method N 24A) : and G. Kessler and H. Lederer, Technicon Symposium, Mediad Inc., New York, Pages 345–347 (1965), respectively. For such usage, the compounds may be administered orally or parenterally, preferably orally, and in admixture with conventional pharmaceutical carriers. The dosage administered may vary depending upon known variables such as the particular compound employed and the severity of the condition being treated. In general, satisfactory results are obtained when administered at a daily dosage of from about 4 milligrams to about 250 milligrams per kilogram of animal body weight, preferably given orally and in divided doses, 2 to 4 times a day, or in sustained release form. For most mammals the total daily dosage is from about 200 milligrams to about 3000 milligrams of the compound, and dosage forms suitable for internal administration comprise from about 50 to 1500 milligrams of the compound in admixture with a solid or liquid pharmaceutically acceptable carrier or diluent.

For above usage, compounds (I) may be administered orally in such forms as tablets, dispersible powders, granules, capsules, syrups and elixirs; and parenterally as solutions, suspensions, dispersions, emulsions, and the like, e.g., a sterile injectable solution such as an aqueous suspension. These pharmaceutical preparations may contain 0.5% up to about 90% of the active ingredient in combination with the carrier or adjuvant, more usually between 3 and 50% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g. starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyetylene stearate and polyoxyethylene sorbitan monooleate) and preservatives (ethyl-p-hydroxybenzoate). Capsules may contain th active ingredient alone or admixed with an inert or solid diluent, e.g., calcium carbonate, calcium phosphate, kaolin, peanut oil, sesame oil and corn oil.

Tablets and capsules containing the ingredients indicated below may be prepared by conventional techniques and are useful in treating lipidemia, particularly hyperlipoproteinemia, in mammals at a dose one tablet or capsule 2 to 4 times per day:

| Ingredient | Weight in Milligrams | | |
|---|---|---|---|
| | Tablet | Capsule | Capsule |
| 3'-(2'-naphthyl)-4,4-dimethyl-pent-1-yn-3-ol | 50 | 50 | 100 |
| Tragacanth | 10 | | |
| Lactose | 197.5 | 170 | |
| Corn Starch | 25 | | |
| Talcum | 15 | | |
| Magnesium Stearate | 2.5 | | |
| Polyethylene Glycol (M.W. 6000) | | | 120 |

The compound 3-(2'-naphthyl)-4,4-dimethyl-pent-1-yn-3-ol is a particularly preferred compound of this invention.

In the following examples, which are illustrative of the invention, temperatures are in degrees centigrade, and room temperature is 20° to 30° C., unless indicated otherwise.

EXAMPLE 1

3-biphenylyl-4,4-dimethyl-pent-1-yn-3-ol

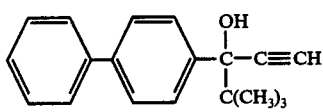

Step A: 4-phenylpivalophenone

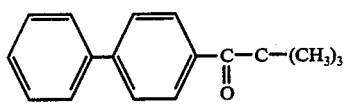

To a 2-liter, four-necked flask, equipped with a stirrer, thermometer, condenser and a dropping funnel is added 13.4 g of magnesium turnings and a small crystal of iodine. The flask is warmed to vaporize the iodine, and to the warmed flask, is added in one portion 30 g of 4-bromo-biphenyl in 100 ml of absolute THF, resulting in a vigorous, but controllable reaction 86 g of 4-bromobiphenyl in 290 ml of absolute THF is added at a rate so as to maintain the reaction at gentle reflux. After the addition is completed, the mixture is refluxed for 45 minutes (resulting in the formation of a Grignard reagent). The thus prepared Grignard agent is transferred to a dropping funnel (under dry nitrogen gas), and slowly added to a mixture of 70 g of trimethyl acetyl chloride in 200 ml of THF. After addition is completed, the mixture is stirred for 1 hour at room temperature. The mixture is then decomposed by dropwise addition of 500 ml of 2N hydrochloric acid. 200 ml of brine (saturated aqueous sodium chloride) is then added with 200 ml. ether and the organic phase separated. The organic phase is washed 3 times with 2N sodium carbonate, dried over anh. S.S.*, filtered and the filtrate evaporated (i.v.) to obtain a residue, from which is obtained 4-phenylpivalophenone, m.p. 94° – 96° C. from ether.

*anhydrous sodium sulfate.

Step B: 3-biphenylyl-4,4-dimethyl-pent-1-yn-3ol

To a saturated solution of acetylene in 1500 ml of abs. THF is added 77 g of lithium acetylide/ethylenediamine complex. A solution of 80 g of 4-phenylpivalophenone in 400 ml THF is added dropwise over a period of 30 minutes, during which time acetylene is bubbled through the reaction mixture. After stirring for 1 hour at room temperature, the reaction mixture is decomposed by dropwise addition of 500 ml. of water, 200 ml. of brine and 200 ml. of ethyl acetate are then added. The organic phase is separated, washed 3 times with 100 ml. portions of distilled water, dried over anh. S.S., filtered and evaporated (i.v.) to dryness to obtain a residue. From the residue is obtained 3-biphenylyl-4,4-dimethyl-pent-1-yn-3-ol, m.p. 154°–155° C., by crystallization from ether/pentane.

EXAMPLE 2

Repeating the procedure of Example 1, but replacing the 4-bromobiphenyl used in Step A, thereof, with an approximately equivalent amount of:
  (a) 2-bromo-6-methoxynaphthalene;
  (b) 1-bromo-4-phenoxybenzene;
  (c) 2-bromonaphthalene; or
  (d) 1-bromo-3-chloro-4-(n-propoxy)-benzene
there is accordingly obtained, respectively, (crystallized from pentane):
  (a) 3-(6'-methoxy-2'-naphthyl)-4,4-dimethyl-penta-1-yn-3-ol; (m.p. 97°–99°).
  (b) 3-(4'-phenoxyphenyl)-4,4-dimethyl-pent-1-yn-3-ol (m.p. 77°–78°);
  (c) 3-(2'-naphthyl)-4,4-dimethyl-pent-1-yn-3-ol (m.p. 69°–72°); and
  (d) 3-[3'-chloro-4'-(n-propoxy)-phenyl]-4,4-dimethyl-pent-1-yn-3-ol.

EXAMPLE 3

4-(6'-methoxy-2'-naphthyl)-5,5-dimethyl-hex-2-yn-4-ol

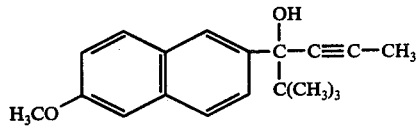

Step A: Methylacetylene Grignard Reagent

A Grignard reagent is prepared by adding to 3.6 g. of magnesium turnings in a vessel, a solution of 12 g. of ethyl bromide in 60 ml. of tetrahydrofuran (THF) dropwise. The mixture begins to reflux during the addition (after about 30 seconds). Addition is continued at a rate so as to maintain a gentle reflux. The mixture is then stirred at room temperature for 1½ hours. The thus-prepared Grignard reagent-containing solution is then added, dropwise, to 200 ml. of THF saturated with methylacetylene. Methylacetylene is bubbled through the reaction mixture during the addition and bubbling continued for an additional 1½ hours after addition of the Grignard mixture is completed to obtain the title alkynyl Grignard reagent. Ethane gas is released from the mixture during the reaction.

Step B: 4-(6'-methoxy-2'-naphthyl-5',5-dimethyl-hex-2-yn-4-ol.

11 g of 1-(6'-methoxy-2'-naphthyl)-tert.butanone in 50 ml THF is added dropwise to the alkynyl Grignard reagent prepared in Step A, above, and the resulting mixture stirred for 16 hours at room temperature. The reaction mixture is then slowly poured into 500 ml. of 2N hydrochloric acid. 200 ml. of saturated aq.sodium chloride and 500 ml. of diethyl ether, are then added. The organic phase is recovered, dried over anh. sodium sulfate, and evaporated to obtain the crude title product as a yellow gum which crystallizes slowly on standing and is refined by triturating with pentane (m.p. 95° to 96°).

Repeating the procedure of this example, but replacing the 1-(6'-methoxy-2'-naphthyl)-tert.butanone used in Step B, with an approximately equivalent amount of 1-(2'-naphthyl)-tert.butanone or 1-(6'-chloro-2'-naphthyl)-tert.butanone, there is similarly obtained:
  (a) 4-(2'-naphthyl)-5,5-dimethyl-hex-2-yn-4-ol; and
  (b) 4-(6'-chloro-2'-naphthyl)-5,5-dimethyl-hex-2-yn-4-ol.

EXAMPLE 4

Following the procedure of Example 1 and utilizing appropriate starting materials there may similarly be prepared:

(a) 3-(p-methoxyphenyl)-4,4-dimethyl-pent-1-yn-3-ol;

(b) 3-(6'-chloro-2'-naphthyl)-4,4-dimethyl-pent-1-yn-3-ol;

(c) 3-(6'-methyl-2'-naphthyl)-4,4-dimethyl-pent-1-yn-3-ol;

(d) 3[4-chloro-(p-biphenylyl)]-4,4-dimethyl-pent-1-yn-3-ol;

(e) 3-(p-lauryloxyphenyl)-4,4-dimethyl-pent-1-yn-3-ol; and (f) 3-(p-isobutylphenyl)-4,4-dimethyl-pent-1-yn-3-ol.

What is claimed is:

1. A compound of the formula

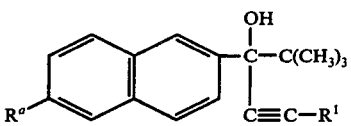

wherein
 $R^1$ is a hydrogen atom or alkyl having from 1 to 4 carbon atoms; and
 $R^a$ is a hydrogen atom, halogen having an atomic weight of from about 19 to 36, alkyl having from 1 to 4 carbon atoms, or alkoxy having from 1 to 4 carbon atoms.

2. The compound of claim 1 which is 3-(6'-methoxy-2'-naphthyl)-4,4-dimethyl-pent-1-yn-3-ol.

3. The compound of claim 1 which is 4(6'-methoxy-2'-naphthyl)-5,5-dimethyl-hex-2-yn-4-ol.

4. A compound of claim 1 in which $R^a$ is a hydrogen atom.

5. The compound of claim 4 which is 3-(2'-naphthyl)-4,4-dimethyl-pent-1-yn-3-ol.

* * * * *